(12) United States Patent  (10) Patent No.: US 8,409,866 B2
Niskanen et al.  (45) Date of Patent: Apr. 2, 2013

(54) APPARATUS AND ASSOCIATED METHODS

(75) Inventors: Antti Niskanen, Cambridge (GB); Jani Kivioja, Cambridge (GB)

(73) Assignee: Nokia Corporation, Espoo (FI)

( * ) Notice: Subject to any disclaimer, the term of this patent is extended or adjusted under 35 U.S.C. 154(b) by 86 days.

(21) Appl. No.: 12/909,049

(22) Filed: Oct. 21, 2010

(65) Prior Publication Data

US 2012/0100626 A1    Apr. 26, 2012

(51) Int. Cl.
*G01N 25/18* (2006.01)
(52) U.S. Cl. ........................................ 436/149; 436/172
(58) Field of Classification Search ........................ None
See application file for complete search history.

(56) References Cited

U.S. PATENT DOCUMENTS

| 6,118,482 | A | 9/2000 | Clark |
| 6,704,447 | B2 * | 3/2004 | Sukthankar et al. ........... 382/170 |
| 2008/0285040 | A1 | 11/2008 | Fourkas et al. ............... 356/445 |

FOREIGN PATENT DOCUMENTS

WO    WO 2007/053092 A1    5/2007

OTHER PUBLICATIONS

Macken, et al., "Towards Integrated Devices for Computer Screen Photo-Assisted Multi-Parameter Sensing", (2008), (6 pages).
Malik, et al., "Imaging Fingerprinting of Excitation Emission Matrices", (2009), (6 pages).
Filippini, et al., "Computer Screen Photo-Excited Surface Plasmon Resonance Imaging", (2008), (8 pages).

* cited by examiner

*Primary Examiner* — Yelena G Gakh
*Assistant Examiner* — Robert Xu
(74) *Attorney, Agent, or Firm* — Harrington & Smith (57) ABSTRACT

An apparatus comprising a processor and memory including computer program code. The memory and computer program code can be configured to, with the processor, cause the apparatus to illuminate one or more sensor elements with electromagnetic radiation emitted from corresponding regions of an electronic display. The one or more sensor elements can be configured to exhibit a specific electrical response to the illumination when a specific set of analytes are bound to the one or more sensor elements, determine the electrical response of the one or more sensor elements, and compare the determined electrical response with one or more predetermined electrical responses to determine a match. Each predetermined electrical response can be associated with the binding of a different set of analytes, wherein determination of a match allows the specific set of analytes bound to the one or more sensor elements to be identified.

19 Claims, 5 Drawing Sheets

APPARATUS AND ASSOCIATED METHODS

TECHNICAL FIELD

The present disclosure relates to the field of optoelectronic sensors, associated methods and apparatus, and in particular facilitates the operation and readout of a plurality of optoelectronic sensors. One or more techniques described herein may or may not be suitable for the detection of impurities, or for health monitoring using portable electronic devices.

BACKGROUND

Optoelectronic sensors can be used to detect the presence of chemical and biological species. This renders them useful for applications in healthcare and environmental monitoring. In order to detect certain medical conditions, however, optoelectronic sensors are required to detect a large number of different species. Performing this analysis sequentially can take a significant amount of time. It would therefore be preferable to determine the presence of all species simultaneously. However, simultaneous detection requires the illumination and readout of a correspondingly large number of heterogeneous sensors, which is currently both complex and expensive.

The apparatus and associated methods disclosed herein may or may not address this issue.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first aspect, there is provided an apparatus comprising:
  a processor and memory including computer program code, the memory and computer program code configured to, with the processor, cause the apparatus to:
  illuminate one or more sensor elements with electromagnetic radiation emitted from corresponding regions of an electronic display, the one or more sensor elements configured to exhibit a specific electrical response to said illumination when a specific set of analytes are bound to the one or more sensor elements;
  determine the electrical response of the one or more sensor elements; and
  compare the determined electrical response with one or more predetermined electrical responses to determine a match, each predetermined electrical response associated with the binding of a different set of analytes, wherein determination of a match allows the specific set of analytes bound to the one or more sensor elements to be identified.

The specific, determined and predetermined electrical responses may comprise one or more of the following: a variation in electrical resistance of the one or more sensing elements, a variation in electrical conductivity of the one or more sensing elements, a variation in output voltage of the one or more sensing elements, and a variation in electrical current flowing through the one or more sensing elements.

The specific electrical response may be caused by absorption of a particular wavelength and/or intensity of electromagnetic radiation by the one or more sensor elements. The absorption of electromagnetic radiation may cause excitation of a plasmon resonance at the one or more sensor elements. Each set of analytes may be associated with a respective disease. The determination of a match may allow the presence or absence of a specific disease to be detected.

Each set of analytes may comprise one or more analytes. Each set of analytes may comprise two or more different analytes. Each analyte may comprise a chemical and/or biological species. Two or more sensor elements may be configured to bind to the same analyte. Two or more sensor elements may be configured to bind to different analytes. At least one sensor element may be functionalised for binding to a specific analyte. The at least one sensor element may be functionalised by the adsorption of a functionalisation molecule onto the surface of the sensor element. At least one sensor element may be a photodetector comprising plasmonic nanoparticles.

Two or more sensor elements may be connected in series or parallel. The apparatus may be configured to determine the combined electrical response of the two or more sensor elements.

The one or more sensor elements may be individually addressable. The apparatus may be configured to determine the electrical response of each sensor element individually.

The electromagnetic radiation may comprise one or more of the following: visible light, infrared radiation, and ultraviolet radiation.

The electronic display may form part of a first device. The one or more sensor elements may form part of a second device. The first and second devices may be configured to be removably attachable to one another. The apparatus may comprise the one or more sensor elements and/or the electronic display. The apparatus may be a portable electronic device, or a module for a portable electronic device.

According to a further aspect, there is provided a method comprising:
  illuminating one or more sensor elements with electromagnetic radiation emitted from corresponding regions of an electronic display, the one or more sensor elements configured to exhibit a specific electrical response to said illumination when a specific set of analytes are bound to the one or more sensor elements;
  determining the electrical response of the one or more sensor elements; and
  comparing the determined electrical response with one or more predetermined electrical responses to determine a match, each predetermined electrical response associated with the binding of a different set of analytes, wherein determination of a match allows the specific set of analytes bound to the one or more sensor elements to be identified.

According to a further aspect, there is provided a computer program, recorded on a carrier, the computer program comprising computer code configured to enable:
  illumination of one or more sensor elements with electromagnetic radiation emitted from corresponding regions of an electronic display, the one or more sensor elements configured to exhibit a specific electrical response to said illumination when a specific set of analytes are bound to the one or more sensor elements;
  determination of the electrical response of the one or more sensor elements; and
  comparison of the determined electrical response with one or more predetermined electrical responses to determine a match, each predetermined electrical response associated with the binding of a different set of analytes, wherein determination of a match allows the specific set of analytes bound to the one or more sensor elements to be identified.

The present disclosure includes one or more corresponding aspects, embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

Figure 1:
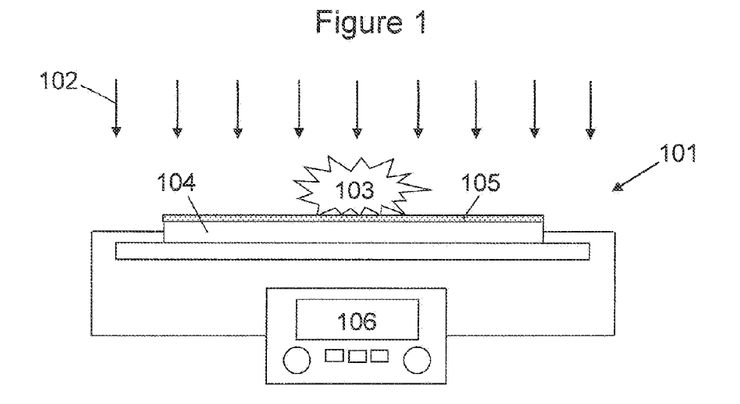
FIG. 1 illustrates schematically an optoelectronic sensor (prior art)

Central to detection is the signal transduction associated with selective recognition of a biological or chemical species of interest. To enable detection of a particular analyte, the electrical response of an optoelectronic sensor element 101 to an illuminating radiation 102 must be dependent on the presence of the analyte 103. The selectivity of a sensor element 101 to a particular analyte 103 can be engineered. One example of a sensor element 101 that satisfies the above criteria is a graphene photodiode 104 which is coated in a layer of plasmonic nanoparticles 105 that have been functionalised (e.g. using a functionalisation molecule) for binding to a specific analyte 103 (as shown in FIG. 1).

The excitation of surface plasmons by electromagnetic radiation is known as a surface plasmon resonance (SPR). This phenomenon forms the basis of many standard tools for measuring adsorption of material onto metallic surfaces, and is behind a variety of biological sensor applications. Surface plasmons (SPs) are surface electromagnetic waves that propagate in a direction parallel to a metal/dielectric interface. Localised surface plasmons (LSPs), on the other hand, are change density oscillations confined to metallic nanoparticles and metallic nanostructures.

A SP is generated when the wavelength of the incident radiation 102 on a plasmonic nanoparticle is in resonance with an eigenmode of the nanoparticle plasmon oscillation. A photodiode 104 which has been coated in a layer of plasmonic nanoparticles 105 is relatively insensitive to all wavelengths of radiation 102 other than the wavelength which is capable of generating a SP. At this critical wavelength, the electrical characteristics (current, output voltage, resistance, and/or conductivity) of the photodiode 104 change dramatically. When the analyte of interest 103 binds to the photodiode 104 via the functionalisation molecule, the plasmon resonance is shifted to a different wavelength. Therefore, by exposing the photodetector to different wavelengths of radiation 102 (e.g. different colours of visible light) whilst measuring the current, voltage and/or resistance (e.g. using a multimeter 106), it is possible to determine whether or not the analyte of interest 103 is present or not.

As mentioned in the background section, the simultaneous detection of a large number of different analytes requires the illumination and readout of a correspondingly large number of heterogeneous sensors, which is currently both complex and expensive. There will now be described an apparatus and associated methods that may or may not overcome this issue.

Figure 2:
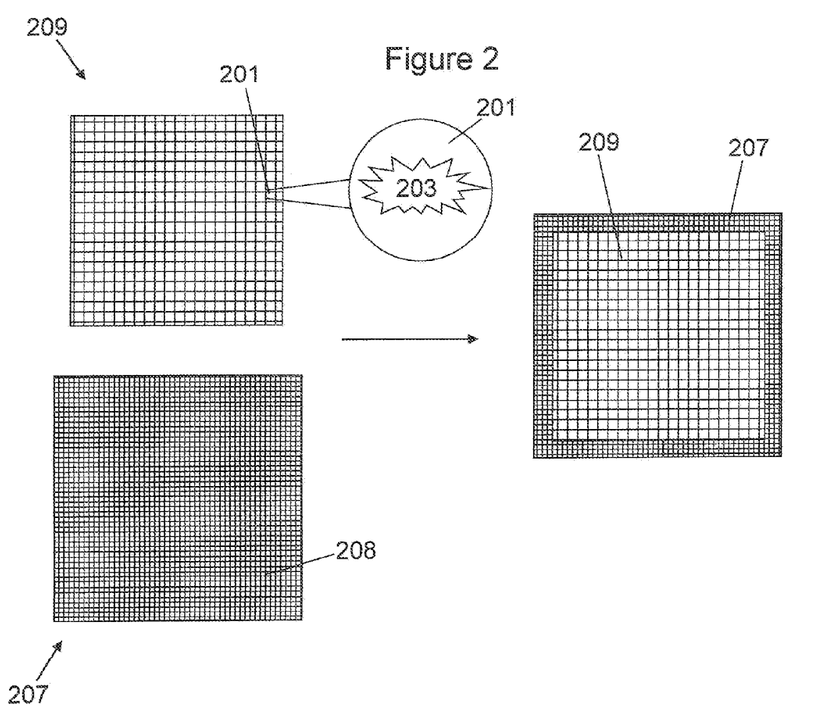
FIG. 2 illustrates schematically a sensor array illuminated using light from an electronic display (present disclosure)

The present disclosure uses the display screen 207 of an electronic device (e.g. mobile phone, PDA or laptop) to illuminate a plurality of sensors 201 simultaneously. The high resolution of modern displays 207, and the ease with which they can be controlled using software stored on the device, renders such displays 207 suitable as candidates for illuminating a plurality of sensor elements 201. Depending on the display 207 resolution and the size and positioning of the sensor elements 201, each pixel 208 on the display 207 may be used to illuminate individual sensor elements 201, or may be used to illuminate a group of sensor elements.

Furthermore, the pixels 208 of modern display screens 207 are typically capable of emitting red, green and blue light. This is particularly useful when the sensor elements 201 are plasmonic photodiodes, because it allows a particular sensor element 201 to be illuminated with light of a specific wavelength, which as described above, is necessary for identifying the presence of the analyte 203.

As well as visible light, the display 207 could be configured to generate other types (wavelengths) of electromagnetic radiation. For example, the display 207 may be configured to generate ultraviolet and/or infrared radiation (possibly as well as visible light). This feature would broaden the range of available wavelengths, and would enable use of sensor elements 201 that are sensitive only to electromagnetic radiation within the ultraviolet or infrared bands.

Another advantage of using an electronic display screen 207 to illuminate the sensor array is that the intensity of radiation (i.e. brightness) can be controlled. In the present case, it would be most beneficial if the intensity of each pixel 208, or groups of pixels, could be controlled independently. This is because the sensitivity of each sensor element 201 to a particular intensity might be different. For example, each sensor element 201 may be configured to detect radiation above a particular threshold (which may be different for each sensor element 201). Below this threshold, the sensor element 201 may be insensitive to variations in wavelength.

In FIG. 2, the sensor elements 201 are arranged in the form of a sensor array cassette 209. Advantageously, the sensor array cassette 209 may be connectable to and disconnectable from the electronic display 207 or the device comprising the electronic display 207. This feature enables the cassette 209 to be manufactured and supplied separately from the electronic display 207 or device (although the sensor array cassette 209 and electronic display 207 or device could be supplied together as a single unit or as a kit of parts). In effect, this allows the cassette 209 to be fitted to existing devices, and allows the cassette 209 to be manufactured and sold at lower cost than a device comprising both the sensor and illumination components. It also prevents consumers wishing to purchase a mobile phone, PDA or laptop etc from having to purchase the sensor array cassette 209 unless they specifically require this additional hardware. Furthermore, if the cassette needs to be modified (e.g. sensor elements added, removed or replaced), repaired or replaced, this can be done without affecting the device itself.

Another important advantage of configuring the cassette 209 to be connectable to and disconnectable from the electronic display 207 or device, is that the biological or chemical specimen under analysis (i.e. the specimen comprising the analytes of interest 203) can be applied to the sensor elements 201 without damaging or soiling the display 207 or device. For example, some biological analytes 203 may be immersed in an aqueous solution. Given that the display 207 and device are electronic in nature, the application of an aqueous solution directly to such a display 207 or device is best avoided to prevent any chance of electrocution of the user, or short-circuiting of the electrical components.

Figures 3A, 3B:
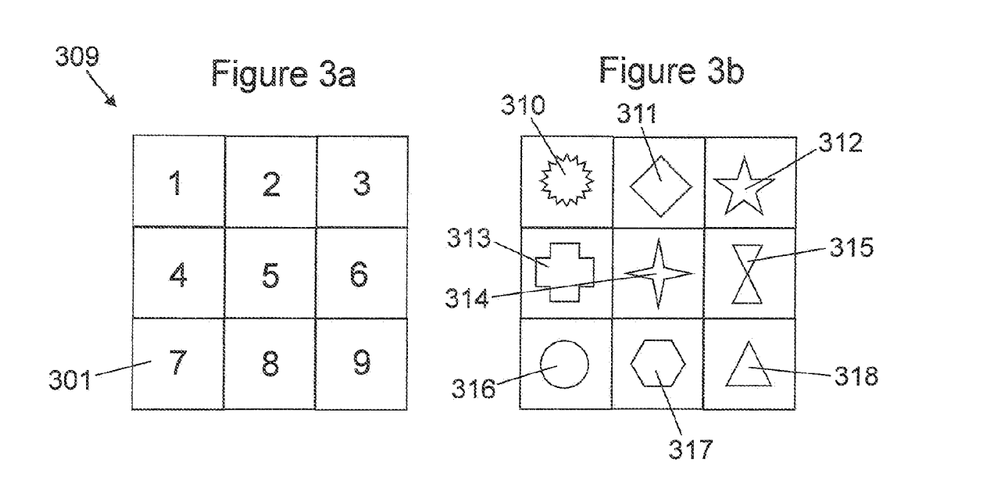
FIG. 3a illustrates schematically a sensor array comprising nine sensor elements, each configured to bind to a different analyte (present disclosure)
FIG. 3b illustrates schematically the sensor array of FIG. 3b after the different analytes have bound to the sensor elements (present disclosure)
Figure 3C:
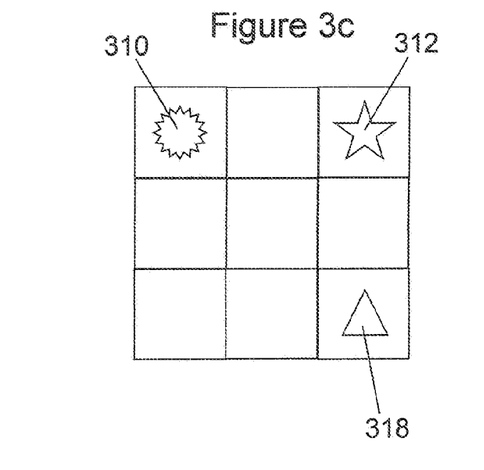
FIG. 3c illustrates schematically an analyte pattern corresponding to a first disease (present disclosure)
Figure 3D:
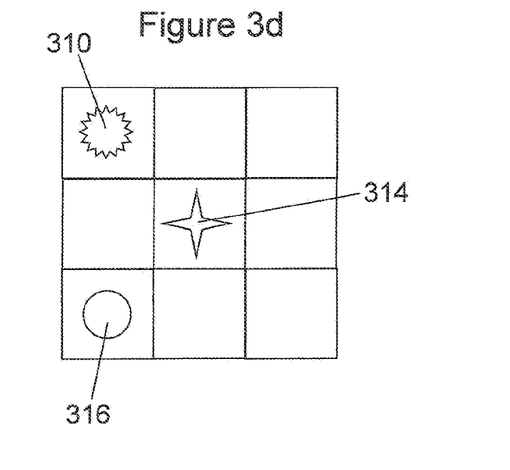
FIG. 3d illustrates schematically an analyte pattern corresponding to a second disease (present disclosure)

The general operation of the above-described apparatus will now be illustrated by describing a disease-detection application with reference to FIG. 3. It should be noted, however, that the apparatus and methods described herein could be applied to a number of different applications, one being the detection of impurities in solution (e.g. impurities in water, oil or battery fluid).

Suppose that we wish to determine whether or not a person has one or both of diseases A and B out of a large number of possible diseases. Now suppose that the presence of each possible disease can be determined by the presence of a specific (unique) set of analytes in the saliva of that person, and not by the presence of one analyte alone (although in practice, a single analyte may be sufficient).

In FIG. 3a, the sensor cassette 309 comprises nine different sensor elements 301, labelled 1-9. Human saliva typically contains a large number of different biological and chemical species, but for simplicity in this example, we will assume that it contains only nine possible species (labelled 310-318 in FIG. 3b). In this case, each of the different sensor elements 301 are functionalised for binding to a different species (analyte).

The first thing that needs to be done is to determine the wavelength and intensity of illuminating radiation required to detect the presence of each analyte 310-318. This may be performed by attaching a specific analyte 310-318 to the associated sensor element 301, varying the illumination parameters to generate a surface plasmon, and measuring the electrical response (current, voltage, resistance or conductivity etc) of the sensor element 301. The specific illumination parameters required to generate the surface plasmon are dependent on the presence of that specific analyte 310-318, and the specific electrical response of the sensor element 301 can later be used as a fingerprint to identify the presence of the analyte 310-318.

For example, in order to excite a surface plasmon when analyte 310 is bound to sensor element 1, it may be necessary to illuminate sensor element 1 with ultraviolet light at a wavelength of 200 nm and a luminous intensity of 1 candela. Excitation of this surface plasmon might produce an output voltage of 12 mV for sensor 1. On the other hand, in order to excite a surface plasmon when analyte 311 is bound to sensor element 2, it may be necessary to illuminate sensor element 2 with yellow light at a wavelength of 575 nm and a luminous intensity of 0.5 candela. Excitation of this surface plasmon might produce an output voltage of 17 mV for sensor 2. These tests should be performed for each analyte 310-318 using sensor elements 1-9, respectively.

The next step is to determine (e.g. from existing knowledge/literature) the specific set of analytes associated with each possible disease. In the present case, let us assume that disease A is known to be associated with analytes 310, 312 and 318, and disease B is known to be associated with analytes 310, 314 and 316. Therefore, if the sensor array cassette 309 was exposed to saliva taken from a person infected with disease A, analytes 310, 312 and 318 contained in the saliva would bind to sensor elements 1, 3 and 9, respectively (as shown in FIG. 3c). Likewise, if the sensor array cassette was exposed to saliva taken from a person infected with disease B, analytes 310, 314 and 316 contained in the saliva would bind to sensor elements 1, 5 and 7, respectively (as shown in FIG. 3d).

Based on this information and the results of the above tests, we can then create specific light patterns using the electronic display to determine the electrical response associated with a specific set of analytes, and therefore a particular disease. For example, given that saliva taken from a person infected with disease A contains analytes 310, 312 and 318, illuminating sensor elements 1, 3 and 9 using the predetermined illumination parameters would result in a specific electrical response from the sensor array (e.g. a total output voltage of 53 mV, say). Similarly, given that saliva taken from a person infected with disease B contains analytes 310, 314 and 316, illuminating sensor elements 1, 5 and 7 using the predetermined illumination parameters would result in a different specific electrical response from the sensor array (e.g. a total output voltage of 104 mV, say). This should be performed for each possible disease. In this way, we build up a collection of specific light patterns and resulting electrical responses (each light pattern and corresponding electrical response being unique for a particular disease). The light patterns and electrical responses can then be stored in a database for use in subsequent sensing experiments, as discussed below.

To determine if a person has any of the recorded diseases, a sample of the person's saliva (although it could be any other type of specimen containing the specific set of analytes) is applied to the sensor array 309. Once the analytes have been given sufficient time to bind to the sensor elements 301, the electronic display is configured to illuminate the sensor array 309 with the first pre-recorded light pattern, and the corresponding electrical response of the sensor array 309 is determined. Following this, the determined electrical response is compared against the database of predetermined electrical responses to find a match. If no match is found, we can conclude that the specific set of analytes associated with that particular disease are probably not contained within the saliva sample, and therefore that the person is probably not infected with that particular disease. The process is then repeated using the second pre-recorded light pattern, the third pre-recorded light pattern, and so on, until we have determined whether or not the person has each of the recorded diseases.

Using the above example, if the electrical response measured after illuminating the sensor array 309 with the light pattern associated with disease A matched the pre-determined electrical response associated with disease A, we could conclude that the person is probably infected with disease A. Furthermore, if the electrical response measured after illuminating the sensor array with the light pattern associated with disease B did not match the pre-determined electrical response associated with disease B, we could conclude that the person is probably not infected with disease B.

Figure 4A:
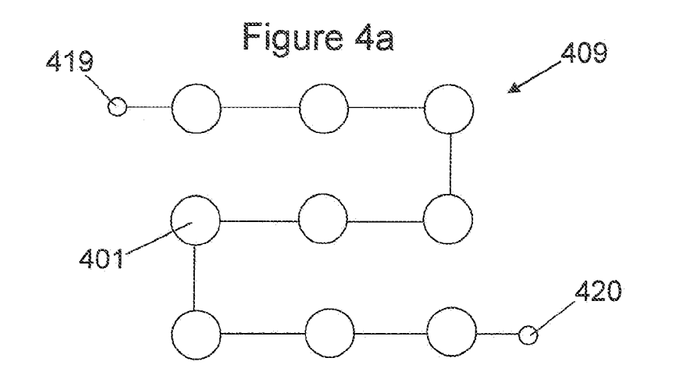
FIG. 4a illustrates schematically a sensor array wherein the sensor elements are connected in series for joint readout.
Figure 4B:
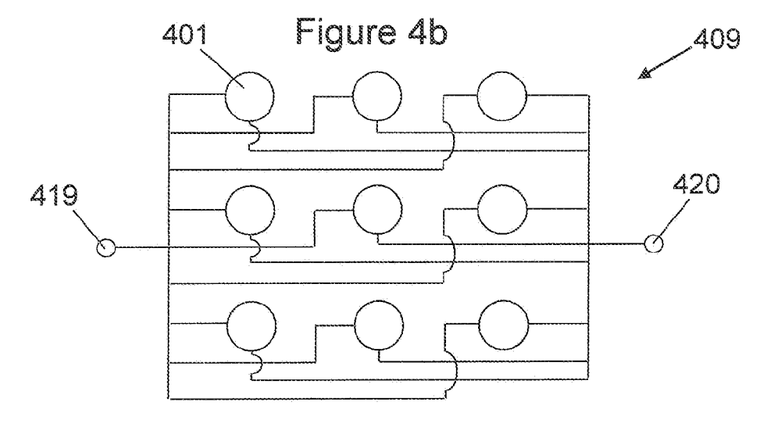
FIG. 4b illustrates schematically a sensor array wherein the sensor elements are connected in parallel for joint readout.
Figure 4C:
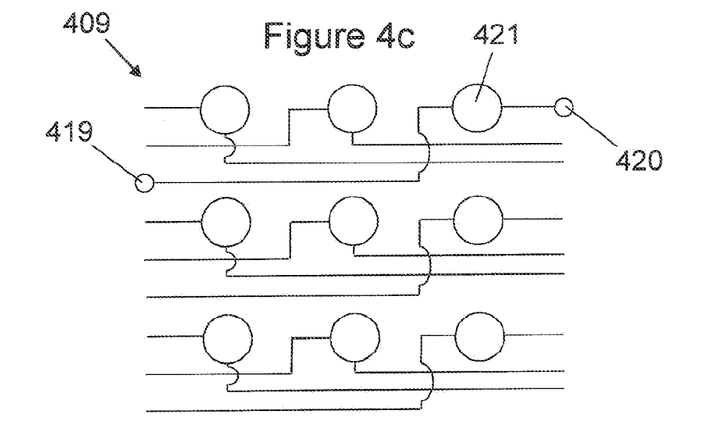
FIG. 4c illustrates schematically a sensor array wherein the sensor elements are individually addressable for independent readout.

The way in which the sensor array is read out is an important consideration. The sensor elements 401 may be electrically connected in series (FIG. 4a) or in parallel (FIG. 4b). This configuration is advantageous in the sense that only two electrical connections 419, 420 are required to read out the complete array 409 in a single step. In practice, if the device was a mobile phone, this type of array 409 could be read out using the audio input and output ports of the phone, or using dedicated electrical connectors (not shown) which attach to the cassette. One issue with reading out the complete array 409, however, is that exactly the same electrical response could conceivably be produced using two or more different light patterns. In this situation, it may be difficult to determine exactly which analytes are present in the sample. This problem may be overcome by configuring the sensor elements 401 such that they are individually addressable (FIG. 4c). In this way, each sensor element 401 can be read out separately by specifying a particular sensor address (e.g. row and column). For example, the electrical characteristics of sensor element 421 at address "1,3" may be determined by connecting the measurement apparatus to electrical connections 419 and 420 as shown in the figure. The disadvantage of this approach, however, is the time it takes to read out each of the different sensor elements associated with a particular disease (e.g. sensor elements 1, 3 and 9 for disease A, or sensor elements 1, 5 and 7 for disease B). In other embodiments, more complex electrical networks may be formed. For example, two or more sensor elements may be connected in series, two or more may be connected in parallel, and/or one or more may be individually addressable, all within the same sensor array.

Figure 5:
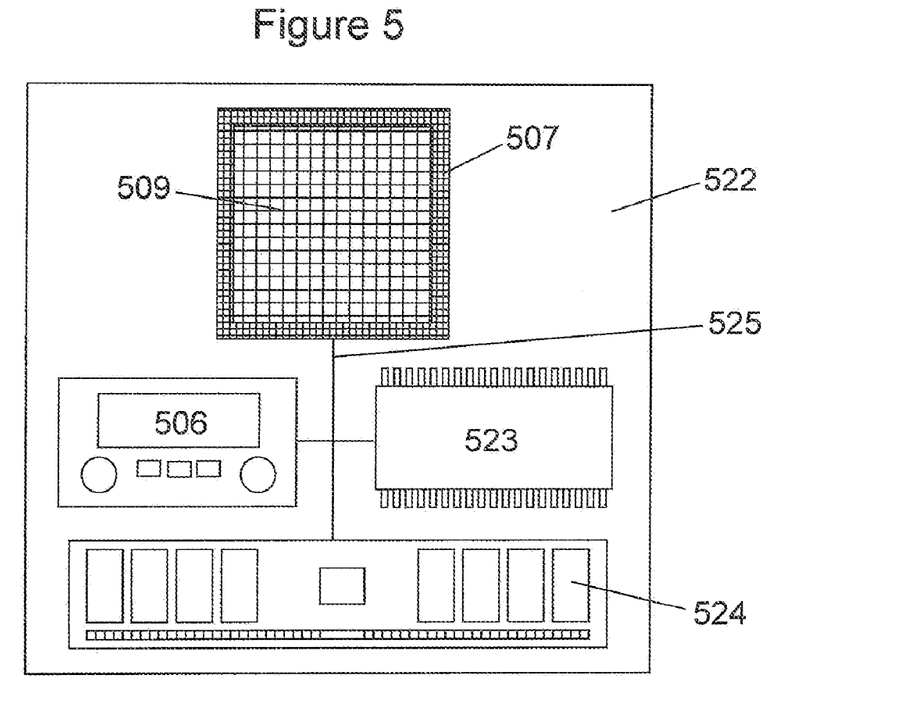
FIG. 5 illustrates schematically a device comprising the apparatus described herein.

FIG. 5 illustrates schematically a device 522 comprising the apparatus described herein. In particular, the device comprises a processor 523, an electronic display 507, a sensor array cassette 509, a measurement apparatus 506, and a storage medium 524, which may be electrically connected to one another by a data bus 525. The sensor array cassette 509 and measurement apparatus 506 may be external components which are attachable to and detachable from the device 522. In addition, the sensor array cassette 509 and measurement apparatus 506 may be manufactured and/or supplied separately from the device 522. The device 522 may be a portable electronic device (such as a portable telecommunications device), or a module for a portable electronic device.

The processor 523 is configured for general operation of the device 522 by providing signalling to, and receiving signalling from, the other device components to manage their operation. The processor 523 is also configured to compare the electrical response of the sensor array 509 with one or more predetermined electrical responses to determine a match and identify the analytes bound to the sensor elements. The speed at which the light patterns (images) are displayed and the electrical responses analysed may be dependent on the power of the processor 523 and/or the amount of device memory 524.

The electronic display 507 is configured to illuminate the sensor array 509 according to one or more stored light patterns by varying the wavelength and/or intensity of individual pixels or groups of pixels. When the different light patterns are displayed consecutively at speed, the electronic display 507 may be considered to be displaying a video. The electronic display 507 may be configured to emit red, blue, green or white light, ultraviolet light, or infrared radiation. The electronic display 507 may also be configured to present the experimental results to the user. For example, once the processor 523 has finished comparing the electrical response of the sensor array 509 with the predetermined electrical responses, the electronic display 507 may present any matches (exact and/or close matches) to the user. The matches may be presented in order of how close the predetermined electrical responses are to the measured electrical response.

The sensor array 509 may comprise one or more sensor elements, which may be electrically connected in series or in parallel. Alternatively, the sensor elements may be individually addressable. The sensor elements may be functionalised (e.g. by the adsorption of functionalisation molecules onto their surfaces) for binding to specific analytes. In some embodiments, more than one sensor element may be configured to bind to the same analyte. This helps to increase the chances of this particular analyte binding to the sensor array. It also provides backup sensors for detection of this analyte when one or more sensor elements are damaged, or when an unwanted analyte has bound to the wrong sensor element, without having to clean, repair or replace the sensor array cassette 509.

One issue with using multiple sensor elements for detecting the same analyte is that the same analyte may contribute to the total electrical response of the sensor array more than once, which could result in an incorrect identification of the analytes. This issue only arises when the sensor elements are configured to be read out in combination (i.e. not when they are individually addressable electrically). The problem may be overcome, however, if the sensor elements are configured such that their electrical response is constant when the sensor element is not illuminated, and differs from this constant value only when the analyte is present and the sensor element is illuminated. In this way, we can activate individual sensor elements optically without the fear of other sensor elements associated with the same analyte adversely affecting the readout. To achieve this, we must first determine the total electrical contribution of the sensor array when none of the sensor elements are illuminated, so that we can later compare this value with the measured electrical response taken when the sensor array is illuminated with specific light patterns.

Furthermore, when we have multiple sensor elements configured for binding to the same analyte, the analyte may be bound to one sensor element but not the others. In this situation, illuminating only one of these sensor elements may not be enough to determine whether or not the analyte is actually present in the sample. One way of addressing this issue is to illuminate a first set of sensor elements, each sensor element associated with a specific analyte, and measure the corresponding electrical response. Following this, we can then illuminate a second set of sensor elements associated with the same specific set of analytes and measure the corresponding electrical response. This process may be repeated for every set of sensor elements associated with the same specific set of analytes. By taking multiple measurements for each set of analytes, we therefore increase the chances of detecting the presence of each analyte.

Whilst the plasmon sensing mechanism is well-suited to optoelectronic sensors, any other sensing mechanism that results in an electrical response which is dependent on the analyte of interest could also be used. These mechanisms may be used instead of, or in addition to, the plasmon sensing mechanism. One possibility is to incorporate fluorescence with plasmon sensing. For example, each sensor element may be configured to bind to a fluorescent species only when the analyte of interest is present. The fluorescent species may be configured to emit light when excited by a particular wavelength and/or intensity of electromagnetic radiation. In this way, by tuning the plasmon resonance to the light, emitted from the fluorescent species, we could determine the presence of the analyte by illuminating the sensor element with electromagnetic radiation of this particular wavelength and/or intensity say, and detecting a characteristic electrical response associated with the resulting plasmon resonance.

In another embodiment, the plasmonic nanoparticles may be configured to bind to the sensor elements only in the presence of the specific analytes. In this embodiment, a surface plasmon, and therefore a change in the electrical response, would only be produced when the analyte was present in the sample.

The measurement apparatus 506 is configured to measure the electrical response of one or more sensor elements in the sensor array 509. For example, the measurement apparatus 506 may be configured to measure the electrical resistance of the sensor elements, the electrical conductivity of the sensor elements, the output voltage of the sensor elements, and/or the electrical current flowing through the sensor elements. In addition, the measurement apparatus 506 may be configured to measure the electrical response of each sensor element individually, or it may be configured to measure the combined electrical response of all sensor elements in the array 509. The measurement apparatus 506 may comprise one or more of an ammeter, a voltmeter, an ohmmeter, or a multimeter.

The storage medium 524 is configured to store computer code required to operate the device 522, as described with reference to FIG. 7. The storage medium 524 is also configured to store the predetermined electrical responses. The processor 523 may access the storage medium 524 to compare the electrical response of the sensor array 509 with the predetermined electrical responses to find a match and identify the analytes. The storage medium 524 may also be configured to store settings for the other device components. The processor 523 may access the storage medium 524 to retrieve the component settings in order to manage the operation of the other device components. The storage medium 524 may be a temporary storage medium such as a volatile random access memory. On the other hand, the storage medium 524 may be a permanent storage medium such as a hard disk drive, a flash memory, or a non-volatile random access memory.

Figure 6:
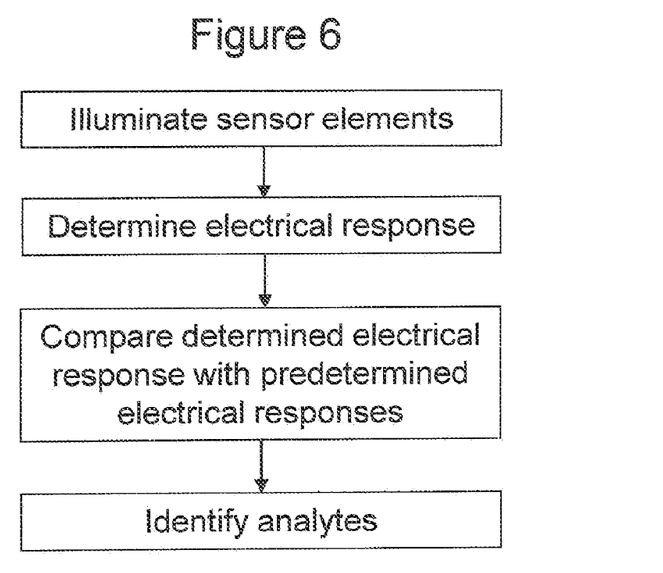
FIG. 6 illustrates schematically a method of operating the apparatus described herein.

The main steps of the method used to operate the device/apparatus are illustrated schematically in FIG. 6.

Figure 7:
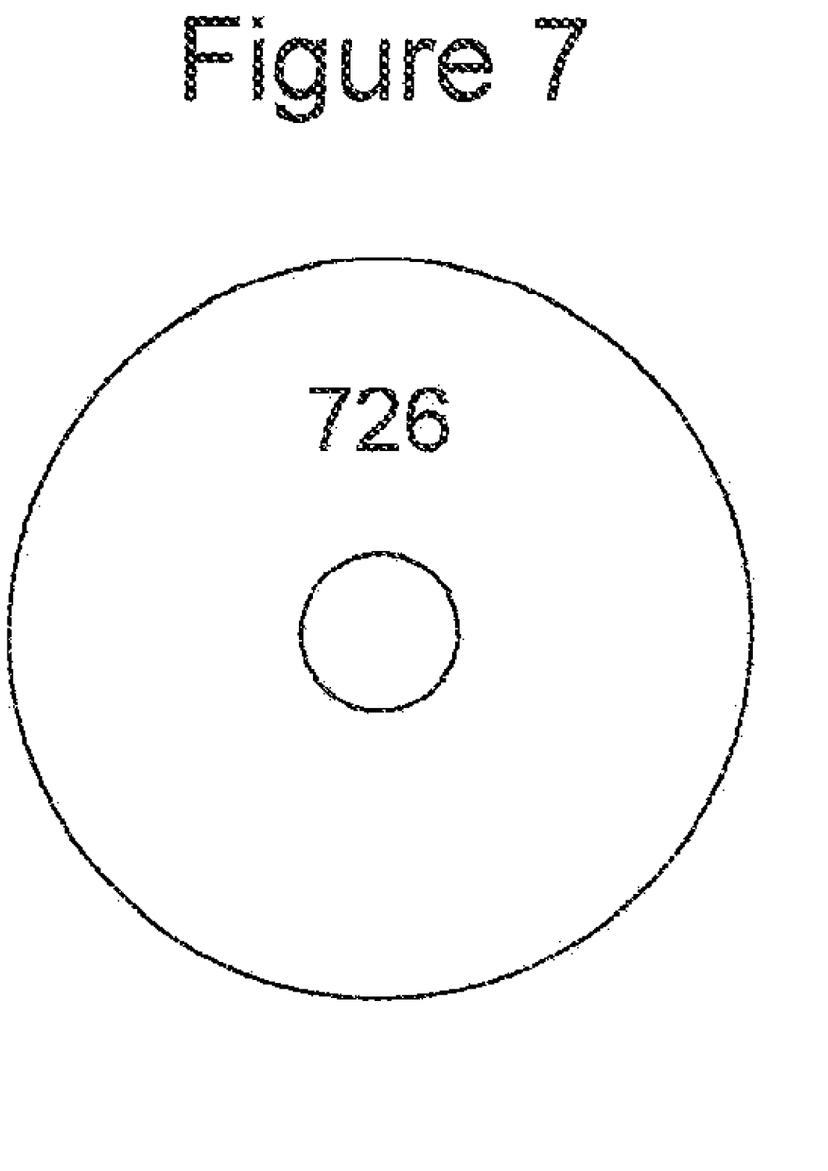
FIG. 7 illustrates schematically a computer readable medium providing a computer program configured to enable operation of the apparatus described herein.

FIG. 7 illustrates schematically a computer/processor readable medium 726 providing a computer program according to one embodiment. In this example, the computer/processor readable medium 726 is a disc such as a digital versatile disc (DVD) or a compact disc (CD). In other embodiments, the computer/processor readable medium 726 may be any medium that has been programmed in such a way as to carry out an inventive function. The computer/processor readable medium 726 may be a removable memory device such as a memory stick or memory card (SD, mini SD or micro SD).

The computer program may comprise computer code configured to enable: illumination of one or more sensor elements with electromagnetic radiation emitted from corresponding regions of an electronic display, the one or more sensor elements configured to exhibit a specific electrical response to said illumination when a specific set of analytes are bound to the one or more sensor elements; determination of the electrical response of the one or more sensor elements; and comparison of the determined electrical response with one or more predetermined electrical responses to determine a match, each predetermined electrical response associated with the binding of a different set of analytes, wherein determination of a match allows the specific set of analytes bound to the one or more sensor elements to be identified.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device/server and/or other features of particular mentioned apparatus/device/server may be provided by apparatus arranged such that they become configured to carry out the desired operations only when enabled; e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device/server may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that the any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
   a processor and memory including computer program code, the memory and computer program code configured to, with the processor, cause the apparatus to:
   illuminate one or more sensor elements of an array of sensor elements with electromagnetic radiation emitted from corresponding regions of an electronic display, the one or more sensor elements configured to exhibit a specific electrical response to said illumination when a specific set of analytes are bound to the one or more sensor elements;
   determine the electrical response of the one or more sensor elements; and
   compare the determined electrical response with one or more predetermined electrical responses to determine a match, each predetermined electrical response associated with the binding of a different set of analytes, wherein determination of a match allows the specific set of analytes bound to the one or more sensor elements to be identified, where
   predetermined groups of sensor elements are illuminated in a predetermined pattern of sensor elements corresponding to predetermined light emitting elements of the electronic display, where an illuminated group of sensor elements comprises fewer than all sensor elements of the array of sensor elements.

2. The apparatus of claim 1, where the specific, determined and predetermined electrical responses comprise one or more of the following: a variation in electrical resistance of the one or more sensing elements, a variation in electrical conductivity of the one or more sensing elements, a variation in output voltage of the one or more sensing elements, and a variation in electrical current flowing through the one or more sensing elements.

3. The apparatus of claim 1, wherein the specific electrical response is caused by at least one of absorption of a particular wavelength and intensity of electromagnetic radiation by the one or more sensor elements.

4. The apparatus of claim 3, wherein the absorption of electromagnetic radiation causes excitation of a plasmon resonance at the one or more sensor elements.

5. The apparatus of claim 1, wherein each set of analytes is associated with a respective disease, and wherein the determination of a match allows the presence or absence of a specific disease to be detected.

6. The apparatus of claim 1, wherein each set of analytes comprises two or more different analytes.

7. The apparatus of claim 1, wherein each analyte comprises a chemical and/or biological species.

8. The apparatus of claim 1, wherein two or more sensor elements are configured to bind to the same analyte.

9. The apparatus of claim 1, wherein two or more sensor elements are configured to bind to different analytes.

10. The apparatus of claim 1, wherein at least one sensor element is functionalised for binding to a specific analyte.

11. The apparatus of claim 10, wherein the at least one sensor element is functionalised by the adsorption of a functionalisation molecule onto the surface of the sensor element.

12. The apparatus of claim 1, wherein at least one sensor element is a photodetector comprising plasmonic nanoparticles.

13. The apparatus of claim 1, wherein two or more sensor elements are connected in series or parallel, and wherein the apparatus is configured to determine the combined electrical response of the two or more sensor elements.

14. The apparatus of claim 1, wherein the one or more sensor elements are individually addressable, and wherein the apparatus is configured to determine the electrical response of each sensor element individually.

15. The apparatus of claim 1, wherein the electromagnetic radiation comprises one or more of the following: visible light, infrared radiation, and ultraviolet radiation.

16. The apparatus of claim 1, wherein the electronic display forms part of a first device, and the one or more sensor elements form part of a second device, and wherein the first and second devices are configured to be removably attachable to one another.

17. The apparatus of claim 1, wherein the apparatus comprises at least one of the one or more sensor elements and the electronic display.

18. The apparatus of claim 1, wherein the apparatus is a portable electronic device, or a module for a portable electronic device.

19. A computer program, recorded on a carrier, the computer program comprising computer code configured to enable:
   illumination of one or more sensor elements of an array of sensor elements with electromagnetic radiation emitted from corresponding regions of an electronic display, the one or more sensor elements configured to exhibit a specific electrical response to said illumination when a specific set of analytes are bound to the one or more sensor elements;

determination of the electrical response of the one or more sensor elements; and comparison of the determined electrical response with one or more predetermined electrical responses to determine a match, each predetermined electrical response associated with the binding of a different set of analytes, wherein determination of a match allows the specific set of analytes bound to the one or more sensor elements to be identified, where predetermined groups of sensor elements are illuminated in a predetermined pattern of sensor elements corresponding to predetermined light emitting elements of the electronic display, where an illuminated group of sensor elements comprises fewer than all sensor elements of the array of sensor elements.

* * * * *